United States Patent [19]

Hewett et al.

[11] Patent Number: 5,171,688
[45] Date of Patent: Dec. 15, 1992

[54] SELF-CORRECTED ASSAY DEVICE

[75] Inventors: Gary E. Hewett, Los Altos Hills; Steven T. Mielke; Judith A. Blunt, both of Fremont, all of Calif.

[73] Assignee: Cholestech Corporation, Hayward, Calif.

[21] Appl. No.: 396,326

[22] Filed: Aug. 23, 1989

Related U.S. Application Data

[63] Continuation-in-part of Ser. No. 238,775, Aug. 3, 1988.

[51] Int. Cl.5 .................. C12M 1/36; C12Q 1/60; G01N 21/00
[52] U.S. Cl. ..................... 435/289; 435/11; 435/28; 422/55; 422/56; 436/164; 436/13
[58] Field of Search ............... 435/7.91, 289, 28, 301, 435/24, 11, 170; 436/510, 164, 13; 422/55, 56

[56] References Cited

U.S. PATENT DOCUMENTS

| 3,607,093 | 7/1973 | Stone . | |
|---|---|---|---|
| 3,791,933 | 2/1974 | Moyer et al. . | |
| 3,907,642 | 9/1975 | Richmond . | |
| 3,907,645 | 9/1975 | Richmond . | |
| 3,925,164 | 12/1975 | Beaucamp et al. . | |
| 3,983,005 | 9/1976 | Goodhue et al. . | |
| 4,038,485 | 7/1977 | Johnston et al. . | |
| 4,042,329 | 8/1977 | Hochstrasser | 436/71 |
| 4,069,017 | 1/1978 | Wu et al. . | |
| 4,125,372 | 11/1978 | Kawai | 436/169 |
| 4,144,129 | 3/1979 | Gruber et al. | 435/11 |
| 4,144,306 | 3/1979 | Figueras | 422/56 |
| 4,153,668 | 5/1979 | Hill et al. | 422/56 |
| 4,164,448 | 8/1979 | Röeschlau et al. | 435/11 |
| 4,181,575 | 1/1980 | Gruber et al. . | |
| 4,186,251 | 1/1980 | Tarbutton | 435/11 |
| 4,212,938 | 7/1980 | Gruber et al. | 435/11 |
| 4,234,317 | 11/1990 | Lucas et al. . | |
| 4,256,693 | 4/1981 | Kondo et al. | 422/56 |
| 4,271,119 | 6/1981 | Columbus | 422/50 |
| 4,391,904 | 7/1983 | Litman et al. | 435/7.91 |
| 4,477,575 | 10/1984 | Vogel et al. | 436/170 |
| 4,503,144 | 3/1985 | Deeg et al. | 435/11 |
| 4,533,629 | 8/1985 | Litman | 435/7.91 |
| 4,544,630 | 2/1985 | Ziegenhorn et al. | 435/11 |
| 4,654,310 | 3/1987 | Ly | 436/164 |
| 4,680,259 | 7/1987 | Cumbo et al. | 435/11 |
| 4,816,224 | 3/1989 | Vogel et al. | 422/55 |
| 4,820,489 | 4/1989 | Rothe et al. | 422/56 |
| 4,826,759 | 5/1989 | Guire et al. | 435/28 |
| 4,826,761 | 5/1989 | Arai et al. | 435/28 |

FOREIGN PATENT DOCUMENTS 0229982 12/1985 European Pat. Off. .
3130749 4/1981 Fed. Rep. of Germany .

Primary Examiner—James C. Housel
Assistant Examiner—William Chan
Attorney, Agent, or Firm—Peter J. Dehlinger

[57] ABSTRACT

An assay device and method for determining the concentration of an analyte in a fluid sample. The device includes a porous-matrix reservoir which receives the sample to be assayed, and at least two reaction zones into which sample fluid is drawn from the reservoir. In an embodiment containing two reaction zones, a single-point standard curve which corrects for reduced-signal effects related to loss of reagent activity and linear inhibition effects, is used to determine analyte concentration. In an embodiment containing three reaction zones, a two-point standard curve which corrects for reduced-signal effects related loss of reagent activity and non-linear inhibition effects, is used to determine analyte concentration. Also disclosed is an apparatus which uses the device for automated or semi-automated analyte assay.

14 Claims, 5 Drawing Sheets

SELF-CORRECTED ASSAY DEVICE

The present invention is a continuation-in-part of U.S. patent application for "Self-Corrected Assay Device and Method," Ser. No. 238,775, filed Aug. 30, 1988.

FIELD OF THE INVENTION

The present invention relates to a method and device for assaying fluid-sample analytes.

REFERENCES.

Aouidet, A., et al., Clin Chem, 29(11):2001 (1983).
Ketterman, R., et al., J Clin Chem Clin Biochem, 22(3):245 (1984).
Kovar, K. A., et al., Clin Chem Acta, 132(3):257 (1983).
Malispina, J. P., et al., Ann Biol Clin, 38(4):207 (1980).
Moshides, J. S., J Clin Chem Clin Biochem, 25(9):583 (1987).
Sharma, A., et al., Clin Biochem, 20(3):167 (1987).

BACKGROUND OF THE INVENTION

Assays for determining a variety of body-fluid analytes in a doctor's office or home setting are available. As a rule, such assays are designed for simplicity of use, on the assumption that the user has little or no training in clinical assay procedures or in reading and interpreting the results of the assay. For this reason, the assays tend to favor one-step analyte addition, with assay results being determined after a reaction end-point is reached. Analyte-addition assays of this type, while convenient for the user, generally lack accuracy and reliability. In particular, the test result may be subject to variations in reaction variables such as reagent levels and activities, particularly where enzyme reagents are involved, and temperature conditions. The accuracy and reliability of many simple assay procedures is also limited by background interference which can vary among analyte samples, and which may also be affected by the condition of the test reagents.

One blood analyte which is frequently assayed in a doctor's office setting, often as part of a cardiovascular examination, is serum cholesterol. Cholesterol is present in the blood either as free cholesterol (about 25%) or in esterified form (about 75%). Total cholesterol levels in normal individual is about 175 mg/dl, although levels as high as 600-700 mg/dl are present in serious hypercholesteremic conditions. It is well established that high blood cholesterol level, and particularly a high level of esterified cholesterol associated with low density lipoproteins (LDL), is directly associated with a number of serious disease conditions in humans, including coronary artery diseases, biliary obstruction, and liver or thyroid dysfunctions.

Cholesterol assays for use in a doctor's office setting are commercially available. However, despite the importance of cholesterol level as an indicator of a number of important disease states, these assays have proven to have limited accuracy and/or reliability, for the reasons discussed above. For example, the patient serum may inhibit color development on the pad, with the result that the cholesterol measurements may be spuriously low. Alternatively, enzyme reagents in the pad may have aged or otherwise denatured, also leading to low readings.

SUMMARY OF THE INVENTION

It is therefore one general object of the invention to provide an analyte test device and method which is both simple and reliable.

Another object of the invention is to provide an apparatus using such device and employing such method to determine an analyte value which is corrected for background effects and determined from a standard curve.

The device of the invention includes first and second reaction zones into which an analyte-containing body-fluid sample is introduced. In a preferred embodiment of the device, the reaction zones are porous-matrix pads designed to draw the fluid sample into the zones by surface wetting. The reactions zones may be in contact with a reservoir which receives and distributes the fluid sample to the zones.

The first reaction zone contains analyte-specific component(s) which are effective, when an analyte-containing fluid sample is added to the zone, to utilize the analyte to produce an intermediate reaction product. Signal-generating component(s) also present in the first reaction zone are effective to utilize the intermediate reaction product to produce a signal product having a measurable value which is dependent on the concentration of analyte present in the fluid sample.

The second reaction zone contains a known amount of a reference compound which is not present in the aqueous fluid sample, and compound-specific component(s) which are effective, when an analyte-containing fluid sample is added to the zone, to utilize the reference compound to produce the intermediate reaction product. Also included in this zone are the above signal-generating component(s). The two-zone device permits determination of analyte concentration based on a standard curve which is connected for background and linear-inhibition effects.

The device may further include a third reaction zone whose reaction components are like those of the second zone, but with a different known amount of reference compound. The three-zone device permits determination of analyte concentration based on a standard curve which is corrected for background and non-linear inhibition effects.

In one preferred embodiment, the analyte-specific reaction component(s) in the first zone, and the compound-specific component(s) in the second zone are effective to react with the analyte and reference compound, respectively, to produce $H_2O_2$. The signal-generating component(s) in this embodiment include a peroxidase and a dye which is converted by the peroxidase, in the presence of $H_2O_2$, to a distinctively colored signal reaction product.

In a device designed for use in determining serum cholesterol, the analyte-specific component(s) include cholesterol ester hydrolase and cholesterol oxidase. The reference compound is preferably a water-soluble D-amino acid, and the compound-specific component(s), the corresponding D-amino acid oxidase.

In another aspect, the invention includes an apparatus for determining the amount of an analyte in an aqueous fluid sample. The apparatus includes an assay device of the type described above, preferably including structure for distributing a fluid sample to each of the reaction zones. The signal value at each zone is measured by a signal detector, typically by optical monitoring. The signal values measured in the second, or second and third zones are used to generate a single- or two-point standard curve, respectively, corrected for background and inhibition effects, and the analyte concentration value is determined from the standard curve.

Also disclosed herein is a method using the device and apparatus of the invention for determination of analyte concentration in a body-fluid sample.

These and other objects and features of the invention will becomes more fully apparent when the following detailed description of the invention is read in conjunction with the accompanying drawings.

BRIEF DESCRIPTION OF THE DRAWINGS

FIG. 11 shows idealized plots of reflectance (R) as a function of reaction with time (t) for a reference-compound reaction in the absence of interfering substances (dotted line) and actually observed (solid line); and FIG. 12 illustrates how a cholesterol reading taken from a internal calibration curve (solid line) is corrected for interfering compounds.

DETAILED DESCRIPTION OF THE INVENTION

A. Assay Device

Figure 1:
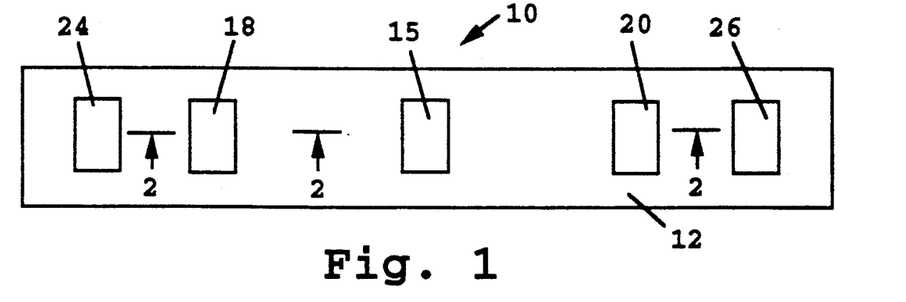
FIG. 1 shows a strip-type assay device constructed according to one embodiment of the invention.

FIG. 1 shows an assay device 10 constructed according to one embodiment of the invention. The device includes a porous-matrix strip 12 formed of a network of fibers, such as fibers 14 seen in FIG. 2. The porous, fibrous network construction is designed to draw fluid applied to the strip by surface wetting through the strip. That is, a fluid sample applied to one zone of the strip will migrate by surface wetting toward opposite ends of the strip until the entire strip is wetted. The fluid sample is applied to a sample pad 15 located at the center of the strip. The pad and the strip are preferably constructed to partially remove unwanted particles, such as blood cells, as the sample fluid migrates through the pad toward the strip.

A variety of fibrous strip materials, such as are used in fibrous-mat filters, including cellulose, cellulose acetate, and glass fibrous matrices, are suitable materials for the strip and sample pad. The fibers may be crosslinked, if desired, by chemical crosslinking, heat fusion, or the like. Also suitable are porous substrates, such as scintered glass, fused polymer beads, and the like whose wettability and dimension of interstices are such as to promote movement of an aqueous medium into the matrix by surface wetting. One suitable material for the pad and strip is glass fiber filter material which acts to separate particles from non-particulate solute material in a fluid sample on the basis of particle size. Thus, for example, a blood sample applied to the pad is drawn through the strip away from the pad, with the concentration of blood particles in the sample decreasing at the leading edge of the migrating sample.

The strip has typical dimensions of about 1-5 cm in length, 4-10 mm in width, and 50-500 microns in thickness. The pad has about the same side dimensions as the width of the strip, and has a thickness between about 5-500 microns.

Figure 2:
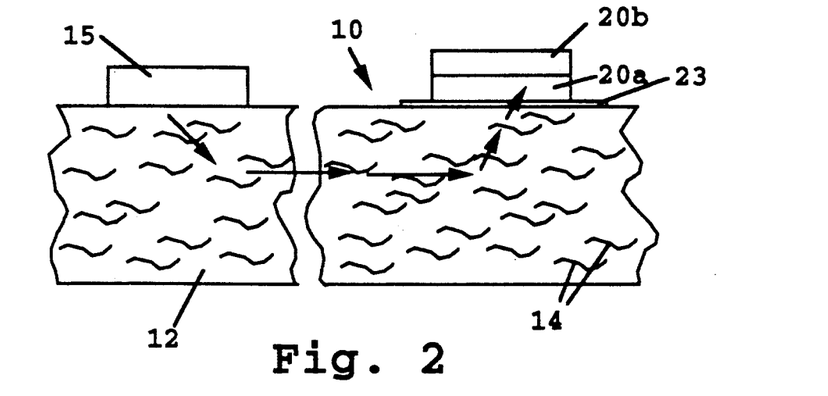
FIG. 2 shows an enlarged sectional view of the FIG. 1 device, taken along line 2—2 in FIG. 1.

Attached to the strip are two reaction pads 18, 20 which are also referred to herein as first and second reaction zones, respectively. These reaction zones are formed of a fibrous matrix filter material, such as described above, designed to draw aqueous fluid by surface wetting. As seen in FIG. 2, pad 20, which is representative, is composed of an inner and outer layers, such as layers 20a and 20b, respectively. The layers in the pad are attached to one another by a conventional fluid-permeable adhesive or the like.

With continued reference to FIG. 2, the pads in the device are attached to and separated from the upper surface of strip 12 by a membrane, such as membrane 23, which is permeable to selected fluid components in the sample fluid, but impermeable to particles or larger solutes in the sample. The size exclusion limit of the membrane is selected to allow passage of desired sample components into the pads, and block undesired material. For example, in an assay device for determination of total serum cholesterol in a blood sample, the size exclusion limit of the membrane is selected to allow passage of lipoprotein particles, such as HDL and LDL particles, but exclude blood cells, such as red blood cells. The membrane is preferably light-colored and opaque, to mask the color effect of filtered red blood cells or the like in the strip below the pad. The pads are attached to the associated membranes, and the membranes are attached to the upper surface of the strip by a conventional fluid-permeable adhesive or the like.

In an assay procedure, a fluid sample introduced on pad 15 at the center of the strip is drawn by surface wetting into strip 12, and from the center of the strip outwardly through associated membranes into two reaction zones, with the concentration of analyte in each reaction zone being essentially the same, since each pad is saturated with the analyte sample fluid. Strip 12 and pad 15 thus serve as a reservoir which provides means for distributing a fluid sample to each of the reaction zones at substantially the same analyte concentration in each zone.

The first reaction zone, i.e., zone 18 in device 10, contains one or more components which are effective to react specifically with the analyte to generate an intermediate reaction product whose concentration is dependent on the concentration of analyte in the zone. The component or components, which are also referred to herein as analyte-specific component means, typically include an analyte-specific enzyme which can react specifically with the analyte to generate the intermediate product or, alternatively, to generate an analyte-related product which can serve as a substrate for a second reaction leading to the intermediate product.

Also included in the first reaction zone are signal-generating component(s) which are effective to utilize the above intermediate reaction product to produce a signal product having a measurable value which is dependent on the concentration of intermediate product in the reaction zone. The component or components necessary to utilize the intermediate product to produce the desired signal product are also referred to herein as signal-generating component means.

The second reaction zone, i.e., pad 20 in device 10, contains a known amount of a reference compound which is not present in the aqueous fluid sample to be assayed, and which is preferably freely soluble in the sample fluid introduced into the zone. The second zone also contains compound-specific component(s) which are effective, when an analyte-containing fluid sample is added to the zone, to utilize the reference compound to produce the above intermediate reaction product. The compound-specific reaction component(s) are also referred to herein compound-specific component means.

Figure 3:
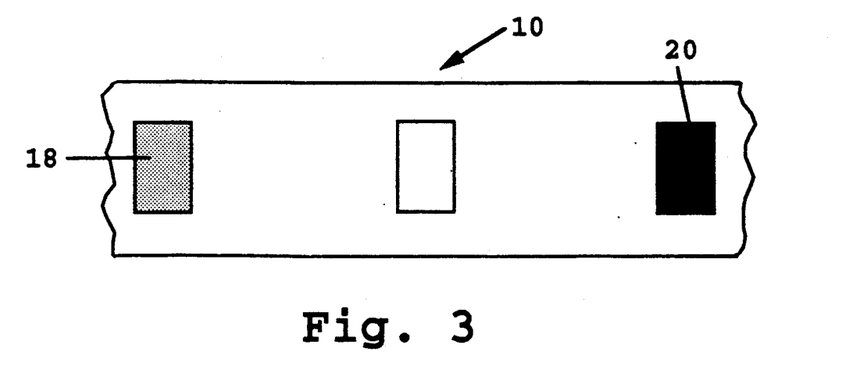
FIG. 3 illustrates a typical color-intensity result achieved with the strip shown in FIG. 1.

In the specific construction shown in FIGS. 1–3, the reference compound and the compound-specific component(s) are contained in different layers 20a and 20b of pad 20, typically with the reference compound being in the lower layer. Thus, as fluid sample is drawn into the pad, the reference compound is dissolved in the sample fluid and carried into the upper layer, where it reacts with the compound-specific components.

Also included in the second reaction zone are the above signal-generating component(s) which are effective to utilize the intermediate reaction product formed by reaction with the reference compound to produce a signal reaction product. The signal-generating components, or component means, are preferably contained in the same dry-layer compartment as the compound-specific-specific component(s).

Exemplary analyte specific component(s), signal-generating companent(s), compound-specific component(s), and reference compound are given in Section B below.

The device shown in FIG. 1 contains two additional reaction pads 24, 26 which provide third and fourth reaction zones, respectively. In one preferred embodiment of the invention, the third reaction zone, i.e., pad 24, includes the same components as the second reaction zone, but a different known amount of reference compound. The amounts of reference compound in the second and third zones are such as to produce different detectable signal product levels, when sample fluid is introduced into the zones, and each at non-saturating signal product levels.

The fourth reaction zone may serve one of a variety of purposes in the analyte assay. In one device, the fourth reaction zone is a duplicate of the first reaction zone, and thus provides a check on the reproducibility and of the assay reaction.

In another embodiment, the fourth reaction zone may contain different analyte-specific component(s) for determining a different analyte, but with the generation of the same intermediate reaction product. As one example, the first reaction zones may contain cholesterol oxidase, for determination of free cholesterol, and the fourth zone, glucose oxidase, for determination of glucose, with both reactions generating the intermediate reaction product $H_2O_2$. As another example, the first reaction zones may contain cholesterol esterase and cholesterol oxidase, for determination of total serum cholesterol, as detailed below, the the fourth zone, cholesterol oxidase only, for determination of free cholesterol, as described below in Section B.

Figure 4:
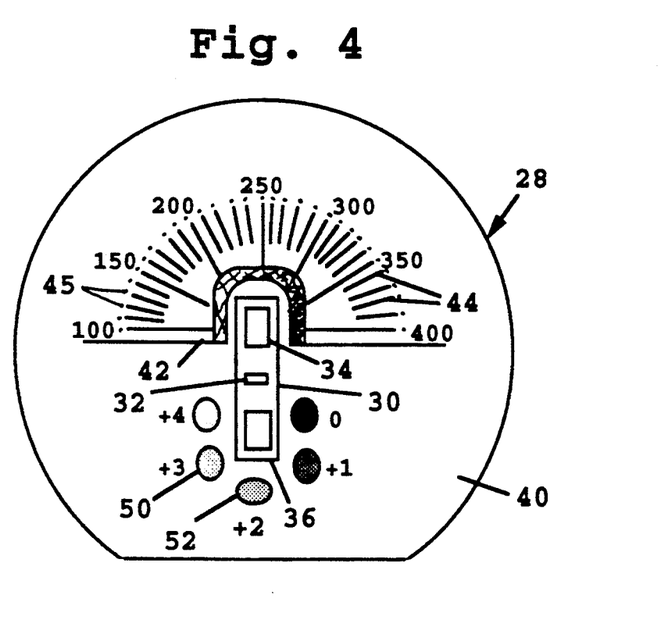
FIG. 4 shows an assay device for use in qualitative analyte determination, in accordance with another embodiment of the invention.

FIG. 4 illustrates an embodiment of an assay device 28 constructed according to another general embodiment of the invention, for use in a qualitative, self-corrected analyte assay. Device 28 is composed of a porous matrix strip 30, similar to above strip 12, a fluid-sample pad 32, similar to above pad 15, and first and second reaction pads or zones 34, 36, having a two-layer construction similar to pads 18, 20, respectively.

The first pad or reaction zone contains the analyte-specific component(s) or component means and signal-generating component(s), or component means, described above with reference to pad 18 in device 10. The first reaction pad is designed to utilize analyte to produce an intermediate product, such as $H_2O_2$, with subsequent reaction to produce the desired signal product.

The second pad or reaction zone contains a reference compound, compound-specific component(s) or component means and signal-generating component(s), or component means, described above with reference to pad 20 in device 10. The second reaction pad is thus designed to utilize reference compound in the pad to produce an intermediate product, such as $H_2O_2$, and utilize the intermediate reaction product to produce the desired signal product.

The strip and attached pads are carried on a plastic card 40 or the like having a variety of indicia and color-intensity markers for use in qualitative determination of analyte concentration. In the device shown, pad 34 is bordered by a color-intensity spectrum band 42 whose increasing color intensity corresponds to increasing analyte concentration values in a typical expected range of values. For example, in a FIG. 4 device, which is intended for cholesterol determination, the color band has an intensity spectrum corresponding to 100–400 mg/dl cholesterol. A plurality of indicia markings, such as marking 44, indicate the corresponding analyte concentration, as indicated. An outer row of dots, such as dots 45, corresponds to 5% increments in concentration values. Thus, the dots immediately to right of the "100," "200," and "300" concentration-value indicia correspond to concentration values of "105", "210", and "315", respectively. The purpose of the dots, for correcting the analyte value determined from the spectrum band 42, will be described below in Section C.

The second reaction zone in the device is surrounded by a plurality of color-intensity markers, such as markers 50, 52, each corresponding to a reference correction value ranging from 0 to +4. The color intensity of the 0-correction color marker is the expected color intensity which is produced under optimal reaction conditions, i.e., without reduction in color intensity due to loss of activity of one or more of the reagents active in color development, or inhibition of the color-generating reactions by the fluid sample added to the pad.

Each successively lower intensity marker corresponds to the color intensity expected with increasing degrees in inhibition and/or loss of enzyme activity. In the embodiment illustrated, each intensity markers corresponds to a decrement in color intensity corresponding roughly to 5%, or a total of 20% inhibition at the +4 marker.

B. Assay Component(s)

The analyte-specific component(s) employed in the first reaction zone typically include an analyte-specific enzyme which is effective to react specifically with the analyte, or an analyte-derived product, and in some cases, analogs of the analyte or analyte-derived products, to generate the above intermediate product. The components in the analyte-specific component means include all of the enzyme, cofactor, and substrate components (other than the analyte itself) necessary to produce the intermediate reaction product in the presence of the analyte.

A wide range of enzymes or enzyme systems which act on selected body-fluid analytes to produce suitable intermediate reaction products are known. Table I shows several exemplary analytes for which suitable analyte-specific oxidases exist. As seen, the analytes may themselves be the substrate of the analyte-specific enzyme, as in the case of glucose, uric acid, amino acid oxidase, and free (non-esterified) cholesterol. Here the analyte-specific oxidase reagents may include only the oxidase enzyme.

Alternatively, the analyte may be first converted by primary analyte-specific enzyme(s) to produce the substrate recognized by the oxidase enzyme. Here the analyte-specific oxidase reagents include both the oxidase and additional enzyme for converting the analyte to the oxidase substrate.

In the case of esterified cholesterol, for example, the analyte-specific oxidase reagents include cholesterol esterase, for converting cholesterol in esterified form to free cholesterol, and cholesterol oxidase, which produces cholestenone and $H_2O_2$ in the presence of oxygen.

The analyte-specific oxidase reagents for determination of serum triglyceride include lipase, which hydrolyses triglyceride to glycerol and free fatty acids; glycerol kinase, which converts glycerol to glycerol-phosphate in the presence of ATP; and glycerolphosphate oxidase, which reacts with glycerol-phosphate to produce dihydroxyacetone-phosphate plus $H_2H_2$.

The analyte-specific oxidase reagents for determination of creatinine include creatinine amidohydrolase, which converts creatinine to urea and sarcosine, and sarcosine oxidase, which converts sarcosine to glycine and formaldehyde, with production of $H_2H_2$.

TABLE I

| Analyte | Substrate | Oxidase |
|---|---|---|
| glucose | glucose | glucose oxidase |
| uric acid | uric acid | uricase |
| amino acid | amino acid | amino acid oxidase |
| free cholesterol | cholesterol | cholesterol oxidase |
| esterified cholesterol | cholesterol | cholesterol oxidase |
| triglyceride | L-glycerol phosphate | L-glycerol phosphate oxidase |
| creatinine | sarcosine | sarcosine oxidase |

It will be appreciated that a variety of other analytes may be assayed by suitable selection of an enzyme or enzyme system capable of reacting with the analyte, with the downstream production of $H_2H_2$ by a suitable substrate-specific oxidase. Alternatively, the analyte may be an oxidase enzyme capable of reacting with a suitable substrate in the oxidase, where the analyte-specific oxidase reagents now include the oxidase-specific substrate, rather than the oxidase enzyme itself.

Another class of enzymes which are suitable for use in the present invention are the dehydrogenases, such as hydroxyacyl dehydrogenase, and various Krebs-cycle dehydrogenases, where the intermediate reaction product is reduced NAD, NADH, or FAD. Since reduced nucleotide cofactors, such as NADH, may be present in the blood-fluid sample, it may be necessary to remove the co-factors prior to introducing the sample into the reaction zone(s). Where the device includes a sample reservoir strip, as described in Section A, the reduced cofactor may be removed catalytically or enzymatically by including suitable immobilized cofactor oxidizing reagents in the pad and/or strip through which the sample migrates, before entering the reaction zone.

A variety of other enzyme systems capable of converting an analyte to an intermediate reaction product which is not present in the analyte-containing fluid sample and which can be converted to a detectable signal product are suitable.

The signal-generating reaction component(s) in the reaction zones typically include one or more enzymes which react specifically with and/or utilize the intermediate reaction product to produce a detectable reaction product. One preferred signal-generating component means suitable for an oxidase enzyme system which produces $H_2H_2$ as an intermediate reaction product includes a peroxidase, and a dye which is converted by the peroxidase, in the presence of $H_2H_2$, to a distinctively colored, signal reaction product. The peroxidase enzyme is a hydrogen-peroxide oxidoreductase, such as horseradish peroxidase, myeloperoxidase, and lactoperoxidase, which catalyses the reaction:

Donor + $H_2O_2$ → oxidized donor + $2H_2O_2$.

The specificity of the enzyme for the donor is generally low, and a number of phenols, aminophenols, diamines, and indolephenols are active. In the present invention, the donor, or substrate reagent, is selected among a variety of known compounds or pairs of compounds which undergo reaction to a detectable, typically chromogenic reaction product as a result of peroxidase-catalysed oxidation.

Exemplary single donor compounds include O-pheylenediamine, amidopyrine (Aouidet), and naphthalene-2,3-dicarboxaldehyde (Malaspina). Typically formation of a colored reaction product involves dimer formation. Examples of donor compound pairs which are suitable include the following primary/secondary compound pairs: 4-aminoanti-pyrine (4AAP)/2-hydroxy-3,5-dichlorobenzenesulfonate (Sharma), which form a red quinoneimine chromophoric compound with an absorption max at 510 nm; 4AAP/phenol (Ketterman); 4AAP/2,4,6-tribromo-3-hydroxybenzoic acid, which forms quinoneimine dye with an absorption max at 515 nm (Moshides); 4AAP/p-hydroxybenzoate, and 3-methylbenzo-thiazolin-2-one hydrazone/3-dimethylaminobenzoic acid, which forms a compound with absorption max at 590 nm (Kovar).

For quantitative determination of analyte, it is, of course, important that the level of signal reaction product which is produced be proportional to initial analyte concentration. This requires first, that the amount of $H_2H_2$ available for formation of signal product be dependent on analyte concentration in the reaction mixture, and secondly, that the amount of reaction product generated also be dependent on the amount of $H_2H_2$ formed. These requirements can be met by employing amounts of analyte-specific oxidase reagents, peroxidase, and substrate reagent which are essentially rate limited only by the amount of analyte introduced initially into the reaction pad. Suitable concentrations of the reagents for use in various oxidase-containing assay systems have been reported (see references cited above). The concentrations of the reagents employed in the serum cholesterol assay device described in the examples below are typical.

Other signal-generating component means are suitable. For example, where the intermediate reaction product is a reduced nucleotide cofactor, the signal-generating components may include a suitable reductase enzyme, such as diaphorase, and a dye which is converted to a reduced form with a distinctive color change.

As indicated above, the reference compound and compound-specific component(s) are selected to produce a predetermined level of signal reaction product, via the intermediate reaction product. The selection of the reference compound is guided by the following requirements: The compound is not present in measurable amounts in the fluid sample introduced into the reference-compound pad. Secondly, the reference compound must be capable of reaction with suitable compound-specific reaction means, with the production of the desired intermediate reaction product. In addition, the reference compound is preferably readily soluble in water, or easily solubilized by detergents or the like which can be included in the reaction zone with interference with the signal-product generating reactions occurring in the zone. One preferred reference compound, in the general embodiment where the intermediate reaction product is $H_2H_2$, is a D-amino acid, such as D-glycine, or D-alanine. The compound-specific oxidase component in this embodiment is the corresponding D-amino acid oxidase.

The assay components just described are preferably included in the associated reaction pad by adding a known volume of assay-component solution to the pad, then dehydrating, e.g., by lyophilization. In the case of the reference-compound pad, a known amount of a solution of the reference compound is introduced into one layer, and a solution of the compound-specific and signal-generating components are introduced into the second layer. After dehydration, the two layers are joined as described above.

One exemplary device, described in Examples 1 and 2, is designed for determination of total serum cholesterol. The analyte-specific reaction components in the first reaction zone include cholesterol ester hydrolase, for releasing cholesterol in free (non-esterified) form from serum lipoproteins, and cholesterol oxidase, for converting free cholesterol to cholestenone and $H_2H_2$. The signal-generating components in the first zone include a peroxidase, and a dye or dyes (see Example 1 below) which changes from clear to colored with pyroxidase-catalyzed oxidation in the presence of $H_2O_2$.

The second reaction zone includes a known amount of D-amino acid, such as D-proline, D-glycine, or D-alanine, and a D-amino acid oxidase (which is reactive with substantially all D-amino acids), and the above signal-generating components for generating the signal product in the presence of $H_2O_2$. Preferred concentrations of the reagents and reference compound are given in Example 1 below.

A three-zone device for analyte determination is similarly constructed, but includes a third reaction zone which contains the same components as the second reaction zone, but a different known amount of reference compound. One illustrative three-zone device, designed for determination of total serum cholesterol, is identical to the device just described, but contains a third reaction zone with a different, predetermined amount of D-amino acid. A fourth reaction zone in the device may contain the same assay components as the first reaction zone, to provide a measure of standard deviation in the device.

Table I below shows the components present in the three reaction zones, and the reactions occurring in each zone:

TABLE I

| Components | Zone 1 | Zone 2 | Zone 3 |
|---|---|---|---|
| Sample (cholesterol esters + free cholesterol) | + | + | + |
| cholesterol esterase | + | | |
| cholesterol oxidase | + | | |
| D-amino acid | | + | + |
| D-amino acid oxidase | | + | + |
| $H_2O_2$ generated $H_2O_2$ | + | + | + |
| peroxidase + | + | + | + |
| dye(s) | + | + | + |
| colored dye | + | + | + |

The test devices just described are designed for assaying total serum cholesterol, that is, cholesterol which is associated with lipoproteins in free (non-esterified form) and cholesterol esters which are associated with lipoproteins. The device may be modified for assaying free cholesterol only, and/or cholesterol esters, by modifying the fourth reaction zone to react with free, but not esterified cholesterol. In this device, the first and fourth reaction zones are identical, except that the fourth zone is lacking in cholesterol esterase. The composition of the four reaction regions is given in Table II below. The manipulation of the four signal values to calculate corrected values of total, free and esterified cholesterol is described in Section C below.

TABLE II

| Components | Zone 1 | Zone 2 | Zone 3 | Zone 4 |
|---|---|---|---|---|
| Sample (cholesterol esters free cholesterol) | + | + | + | + |
| cholesterol esterase | + | | | |
| cholesterol oxidase | + | | | + |
| D-amino acid | | + | + | |
| D-amino acid oxidase | | + | + | |
| generated $H_2O_2$ | + | + | + | + |
| peroxidase | + | + | + | + |
| dye | + | + | + | + |
| colored dye | + | + | + | + |

C. Two-Zone Self-Corrected Assay Method

The method described in this section uses a two-zone assay device in a self-corrected assay method. The analyte determination made according to this method may be either qualitative, based on the color intensities of the two zones determined visually by the user, or quantitative, based on a quantitative signal value determination made by conventional reflectance intensity measurements or the like. as described in Section E below.

Describing first a two-zone assay using the device illustrated in FIGS. 1-3, a body-fluid sample, such as a whole blood sample, is applied to pad 15, from which the sample is drawn from the strip into the two reaction zones. In the case of a blood sample, particulate material in the sample, such as blood cells, is filtered, and only cell-free serum is drawn into the pads.

FIG. 3 illustrates a typical reaction result, where the different levels of shading in pads, 18 and 20 represent different final levels of signal reaction, after the pad reactions have gone substantially to completion. The amount of signal product in each pad may be determined quantitatively by a number of known optical methods, such as optical-beam reflectivity, as described below, and may involve time-dependent kinetic measurements rather than as end-point measurements.

Figure 5:
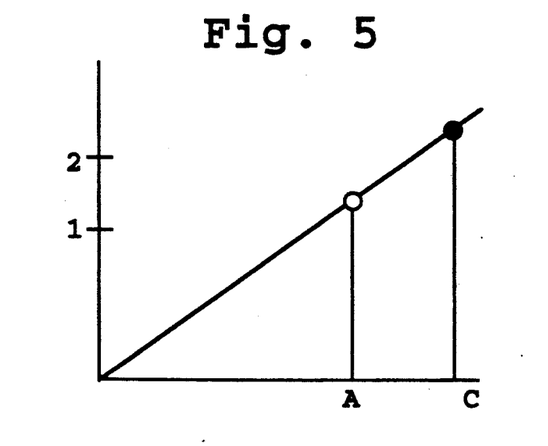
FIG. 5 shows a signal/concentration plot used in calculating analyte concentration from a single-point standard curve, in accordance with the method of the invention.

The measured values are used to calculate a self-corrected analyte concentration, using the steps outlined below and illustrated in the plot in FIG. 5. The reference-compound signal level measured in the second reaction zone, indicated at 2 on the ordinate in the FIG. 5 plot, corresponds to a known concentration of analyte, indicated at C along the abcissa in the figure. The single-reference-compound value is used to establish a single-point standard curve extending from the origin of the plot, as shown.

A corrected analyte value is now determined by plotting the measured signal value from the first reaction zone on the standard curve, and reading the corresponding analyte concentration on the plot, indicated at A in FIG. 5. It will be appreciated that the analyte concentration is self-corrected for reduced signal effects due either to inhibition of the common signal-generating components in the two reaction zones, and/or los of enzyme activity in this system.

More generally, the reduction in signal value observed in the second reaction zone will also apply to that observed in the first reaction zone to the extent that:

(a) sample inhibition or loss of activity effects are confined to the common signal-generating component(s) in each reaction pad, or (b) any sample sample-inhibition or loss of activity effects which apply to the signal-generating component(s) apply equally to the analyte-specific components in the first reaction zone and the compound-specific component(s) in the second reaction zone.

A method for qualitative determination of analyte concentration using the two-zone device described with respect to FIG. 4 will now be considered. As above, a body fluid sample is applied to the center sample pad from which it migrates into first and second zones 34 and 36, respectively. After a given reaction period, preferably at the reaction end point, the signal value—in this case, color intensity—is matched with the a color intensity region of the intensity spectrum band 42, to determine an uncorrected analyte concentration, expressed for example, in mg analyte/dl sample fluid.

At the same time, uptake of fluid sample into the second pad triggers a signal reaction product reaction whose final color intensity is dependent on the amount of reference compound in the pad, and which may be reduced by sample-inhibition effects and/or loss of reagent activity. As noted in Section A above, the percent inhibition or reduction of the signal level can be qualitatively assigned a color-intensity value from 0 to +4, corresponding to an decrease in maximum expected signal value from 0 to 20%, respectively. This percent reduction in color intensity will approximate the percent reduction observed in the first zone, subject to the factors discussed above.

After determining uncorrected the analyte concentration from the first zone reading, the assay value is corrected by (a) locating the dot on the outer ring of the concentration indicia closest to the uncorrected value indicia, (c) advancing 0-4 dots to the right, corresponding to the correction value determined from the second reaction zone, and (c) determining the concentration closest to the final dot advanced to. This procedure has the effect of adding to the uncorrected analyte value, a percent increase which approximately offsets the percent of inhibition observed from the second reaction zone.

By way of illustration, assume that an uncorrected analyte concentration value of "270", and an inhibition level of "+3" are determined initially from the two reaction zones. The user than selects the dot closest to the "270" indicium, advances, three dots to the right, and selects the indicium closest to the last dot—given a corrected analyte concentration value in this case of "310". This is the value that would have been measured, approximately, in the absence of inhibition effects.

D. Three-Zone Self-Corrected Assay Method

A second general embodiment of the assay method of the invention is based on a standard curve generated by two reference value determinations. The method uses the assay device described above in which second and third reaction zones produce two distinct positive reference values when sample fluid is added to the device. As will be seen with reference to FIG. 6 below, this embodiment of the method corrects not only for background signal level, but also compensates for competitive and noncompetitive enzyme inhibition effects.

Figure 6:
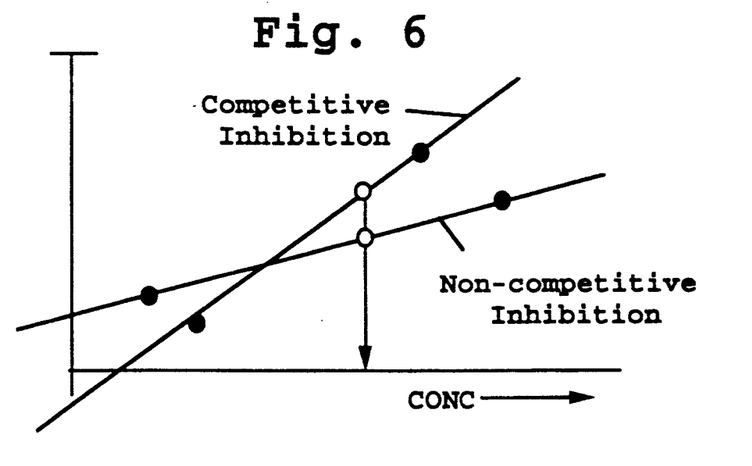
FIG. 6 shows a signal/concentration plot used in calculating analyte concentration from a two-point standard curve in accordance with another embodiment of the method of the invention.

FIG. 6 shows plots of two-point competitive and non-competitive inhibition curves, where each plot is constructed by drawing a straight line through the two reference-value points (solid circles) determined from the second and third reaction zones in the assay device. As seen, competitive inhibition is characterized by decreasing inhibition at greater substrate concentrations, and a negative intercept at the zero-substrate concentration, reflecting the level of inhibition at zero-substrate concentration.

Non-competitive inhibition, by contrast, is characterized by a zero intercept at the zero-substrate concentration, and a progressively greater inhibition at higher substrate concentrations. Although it is possible, using standard curve-fitting methods, to construct the non-linear plot shown at dashed lines in the figure, the curve can be approximated, in the zone between the two reference-value points (solid circles), by a straight line plot drawn between the points.

The first zone gives an analyte concentration value which is uncorrected for background or competitive inhibition. This value is plotted on standard two-point curve (open circle) and the corresponding analyte concentration is read from the intercept with the abscissa (concentration).

According to an important feature of this method, the analyte value determined from the intercept is corrected for both background and enzyme inhibition effects. The background correction is inherent from the fact that first, the same signal value attributable to background is present (or assumed to be present) in each of the three readings, and second, that the two reference points are plotted according to known concentrations of reference compound, and are thus both corrected for background effects. The effect of non-competitive inhibition is corrected inherently by the linear plot, assuming the same degree of non-competitive inhibition is present in each reaction zone.

A first exemplary method, for determination of total serum cholesterol, will be described with respect to signal value plot shown in FIG. 7. The device used in the method has the four-zone construction shown in FIG. 1, where the first three zones contain the reaction components shown in Table I, and the fourth, the same components as the first zone. That is, the first and fourth zones are designed to measure total serum cholesterol in duplicate, and the second and third zones are designed to provide two different reference point signal values.

The method is carried out as above, by adding a blood sample to the central pad, and allowing the filtered serum sample to be drawn up into each of the four reaction zones. At intervals during the reaction, and/or when the reaction in each pad has run substantially to completion, the color intensity of each pad is measured, e.g., by optical-beam reflectivity measurement.

Figure 7:
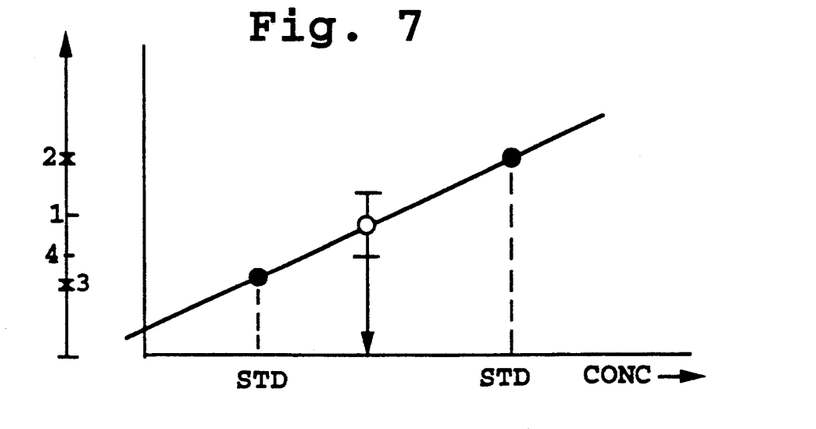
FIG. 7 illustrates the use of a four-zone assay method for determination of total serum cholesterol.

Measured signal values for each of the four zones are shown at the line to the left in FIG. 7. The second and third measurements, which represent different amounts of reference compound corresponding to different preselected cholesterol concentrations, indicated at "STD" in the figure, are used to generate the two-point standard curve shown in the figure.

The first and fourth signal measurements, which represent duplicates of the total cholesterol value, are averaged, and the average value (represented by an open circle) is plotted on the standard curve, and the corresponding cholesterol concentration is read from the curve.

A second exemplary method, for determination of free and total serum cholesterol, will be described with respect to signal value plot shown in FIG. 8. The device used in the method has the four-zone construction shown in FIG. 1, and the four reaction zones contain the reaction components shown in Table II above. The method is carried out as above.

Figure 8:
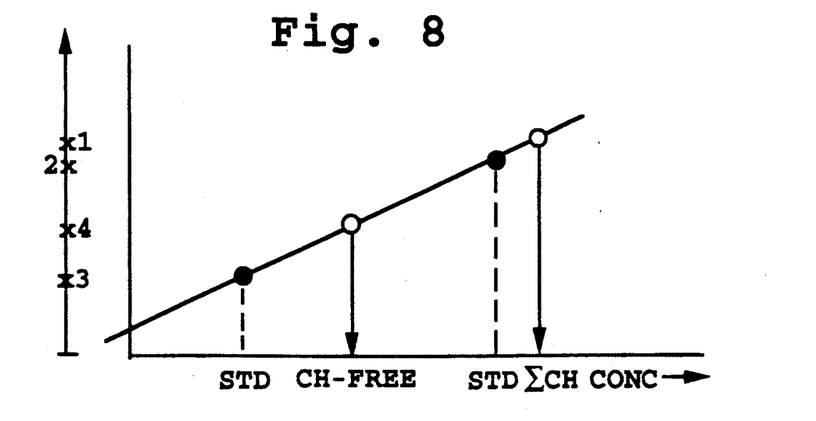
FIG. 8 illustrates the use of a four-zone assay method for determination of total and free serum cholesterol.

Measured signal values for each of the four zones are shown at the line to the left in FIG. 8. The second and third measurements are used, as above, to construct standard plot shown in the figure. The first and fourth reaction zones, which correspond to the signal values produced for total cholesterol (first zone) and free cholesterol only (fourth zone) are then determined by plotting each value on the standard curve, as shown.

In both of the examples above, the three-zone assay method gives an analyte value which is (a) determined from a standard curve and (b) corrected for competitive or non-competitive inhibition effects, and for reduction in signal activity due to loss of reagent activity in the reaction pads. In addition the first method described provides a measure of the reliability of the assay.

E. Assay Apparatus

Figure 9:
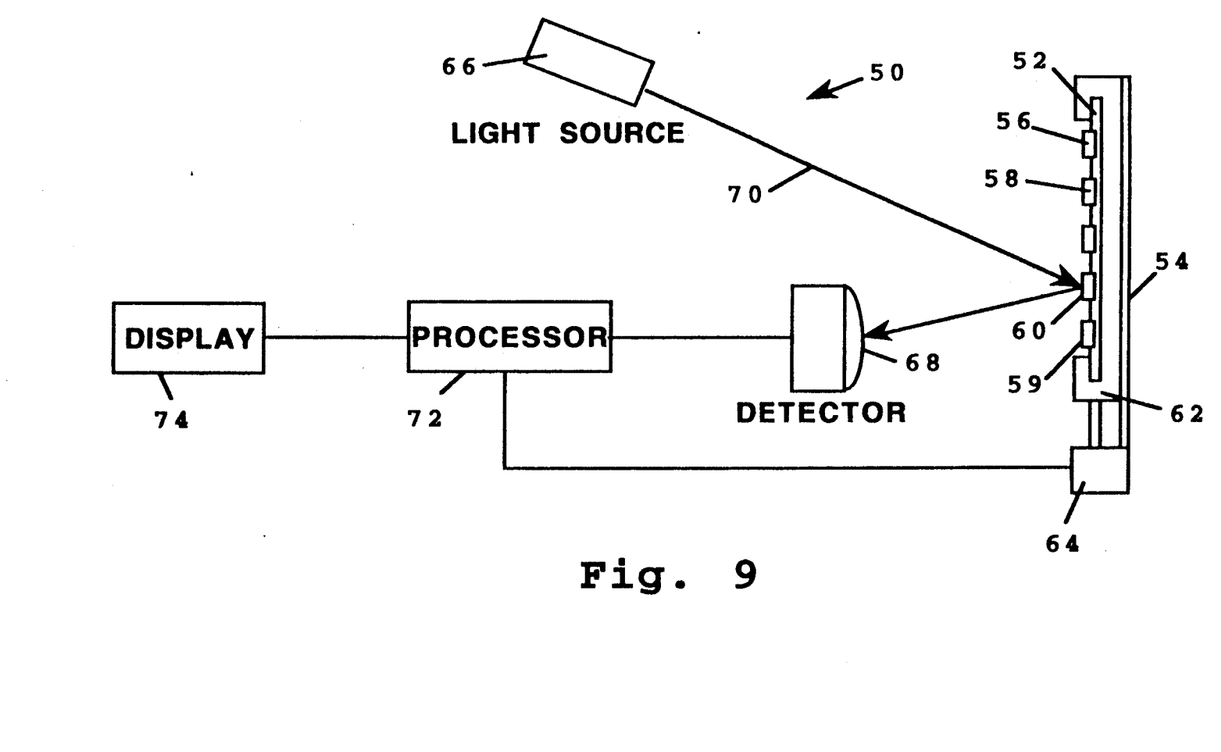
FIG. 9 is a schematic view of an assay apparatus constructed according to the present invention.

In another aspect, the invention includes an apparatus for determining the amount of an analyte in an aqueous fluid sample. FIG. 9 shows a simplified, schematic view of an apparatus 50 constructed in accordance with the invention.

The apparatus includes an assay device 52 which is similar to that described in FIG. 1, and which includes a strip 54 and first, second, third and fourth reaction zones 6, 58, 59, and 60, respectively. Also included in the apparatus is a device holder 62 which is slidable, under the control of an actuator 64, to place the reaction zones at a measurement position occupied by zone 60 in the figure.

In the apparatus illustrated, the level of signal product is measured by reflectance spectroscopy. Means for measuring the signal value in this embodiment includes a light source 66 and a reflected-light detector 68.

Source 66, which directs a focused selected-wavelength light beam 70 at the measurement position may be a low-power laser, a monochromatic, non-coherent light source whose beam is focused by a suitable lens arrangement, an LED, or the like. Detector 68 is a conventional light sensor, such as a photovoltaic sensor, which outputs a light intensity signal value.

The signal values from detector 68 are supplied to a digital processor 72 which carries out the signal-value operations described in Section C. The processor, which is also referred to herein as calculation means, is preferably designed for automated signal measuring operations, through control of actuator 64. These operations are shown in flow diagram form in FIG. 10. Initially, the actuator is controlled by the processor to place the four reaction zones successively at each reaction zone, where the signal value is read and stored by processor memory (not shown).

Figure 10:
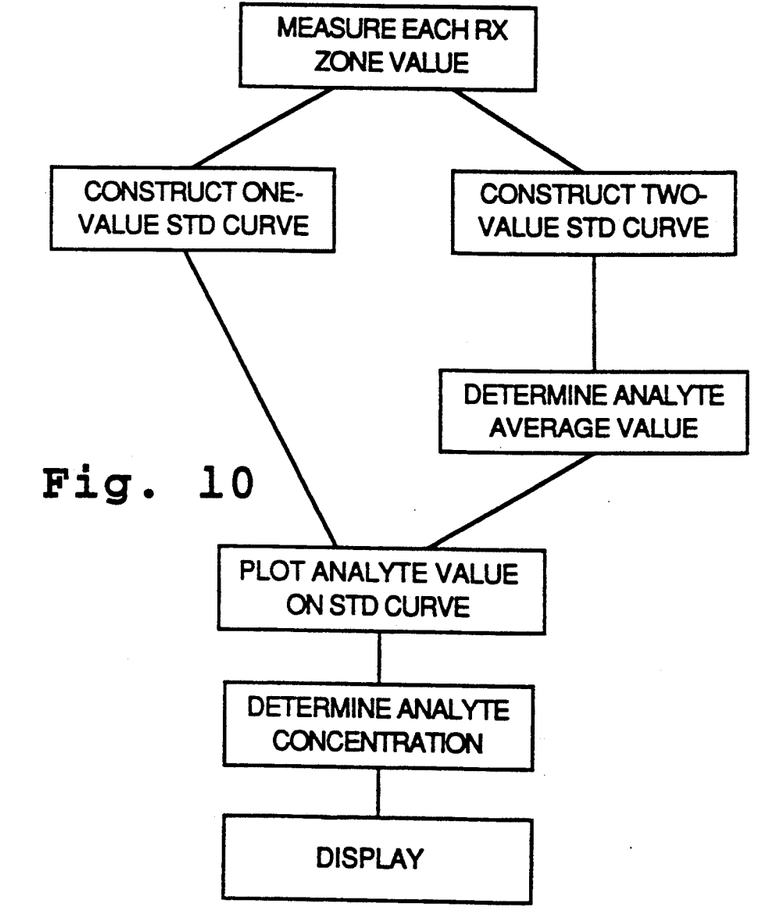
FIG. 10 is a flow diagram of operations performed by the processor in the FIG. 9 apparatus, for determining total analyte concentration using the single-point and two-point standard curve methods of the invention.

The algorithm steps shown at the left in FIG. 10 are employed in the two-zone method above, where the first reaction zone provides a measure of analyte concentration, and the second zone, a measure of reference signal value. The steps performed by the algorithm involve (a) constructing a single-point standard curve from the second-zone value, (b) plotting the first-zone value on the standard curve, (c) determining analyte concentration from the standard-curve plot, and (d) displaying the desired analyte concentration value.

The algorithm steps shown at the right in FIG. 10 are employed in a four-zone method above, based on a two-point standard curve, and a duplicate analyte determination. The steps performed by the algorithm involve (a) constructing a two-point standard curve from the second-and third-zone value, (b) calculating the average first- and fourth-zone values, (c) plotting the average analyte signal value on the standard curve, (d) determining analyte concentration from the standard-curve plot, and (e) displaying the desired analyte concentration value.

Processor design capable of controlling the sample holder, digitizing and storing measured reflectivity values, and carrying out the mathematical operations used to generate the standard curve functions and analyte concentration determinations from the standard curve would be well known to one skilled in the art.

The following example illustrate the use of the method for qualitatively determining total serum cholesterol. The examples is intended to illustrate, but not limit, the scope of the invention.

EXAMPLE 1

Determining Serum Cholesterol: Two-Zone Method

An assay device like that described in FIG. 1 is prepared as follows. A 150 micron thick paper filter obtained from Schleicher and Schl is cut into 2×4 mm rectangles. One of these rectangles, which form the upper layer of reaction zones of the device, is infused with 10 μl of a reagent solution containing 150 U/ml cholesterol ester hydrolase, 10 U/ml cholesterol oxidase, 80 U/ml peroxidase, and 20 mM 4-aminoantipyrine (4-AAP) and 80 mM 3,5-dichloro-2-hydroxybenzoic acid (DCHBS) dye, in reduced form, in deionized water. The lower layer in each reaction zone is formed of an identical-size rectangular piece cut from an 50 micron thick glass fiber filter obtained from Gelman. This layer is infused with 10 μl 0.15 mM proline.

A second rectangle is infused with 10 μl of a reagent solution containing 25 U/ml D-amino acid oxidase, 80 U/ml peroxidase, and 20 mM 4-aminoantipyrine (4-AAP) and 80 mM 3,5-dichloro-2-hydroxybenzoic acid (DCHBS) dye, in reduced form, in deionized water. A second, lower layer is infused with 10 μl 0.15 mM D-proline, as above.

After drying under reduced pressure, the layers are placed against the associated upperlayer rectangles, and the two reaction zones are attached to opposite sides of a 50 micron thick 6×20 mm strip of glass fiber filter obtained from Whatman, and separated therefrom by a 1 micon pore size polycarbonate membrane.

A whole blood sample from a human test subject is obtained conventionally, and applied to the strip in an amount sufficient to wet the three reaction zones on the strip. The strip is incubated at room temperature for 90 seconds, or until no further color development is observed.

The analyte-related signal is read by reflectance spectrophotometry, at an illuminating wavelength of 500 nm. The values for the second reaction zone are compared with signal values obtained by infusing physiological saline into the second zone, i.e., where inhibition by serum components is avoided, and the percent inhibition due to serum-component inhibition is determined. This correction reading is illustrated in FIG. 11 which shows reflectance (R) as a function of reaction time (t) for reference-compound signal values obtained int eh absence of interfering compounds (dotted line), and actually observed in the second reaction zone (solid line). The difference in values at a selected time t' (which could also be a reaction end point) gives the percent inhibition produced by interfering substances in the serum sample, and is indicated by the vertical arrow in the figure.

The values from the first reaction zone are used to determine serum cholesterol concentration, from a predetermined standard curve prepared by adding a predetermined volume of known-concentration solution of cholesterol in non-ionic detergent to reaction pads having the same components as the first reaction zone. The cholesterol concentration calculated from the curve is then corrected for serum inhibition effects using the second-zone inhibition value. This operation is illustrated in FIG. 12, which shows a standard calibration curve of reflectance plotted as a function of cholesterol concentration. An uncorrected cholesterol value is determined by plotting the measured R value for the first reaction zone on the ordinate of the plot, and determining cholesterol value from the calibration curve, as shown. To obtain a cholesterol value corrected for interfering substances in serum sample, the percent inhibition from the reference compound reading is added to the cholesterol reading, as shown, to give a corrected reflectance value. This corrected value is plotted on the calibration curve to give a corrected cholesterol value, as shown.

EXAMPLE 2

Determining Serum Cholesterol: Three-Zone Method

The assay device is similar to that employed in Example 1, except that the three reaction zones contain the components shown in Table II above. The serum sample is introduced, and the reaction signal values are measured as in Example 1.

The values for the first, second, third and fourth reaction zones (labeled 1, 2, and 3, respectively, at the left in FIG. 8), are measured at 500 nm as above. The second and third zone signal values are plotted at corresponding reference-compound concentrations, as indicated in FIG. 8, yielding a standard curve which here indicates non-competitive inhibition. The signal value from the first zone is plotted on this curve, and the corrected analyte concentration is read from the corresponding position on the concentration axis.

A fourth reaction zone contains all of the components of zone 1 except cholesterol esterase. The signal value from this zone thus reflects free serum cholesterol only, since esterified cholesterol in the fluid sample is not released for use. The signal value from this zone is plotted on the two-point standard curve, as indicated in FIG. 8, to determine analyte concentration for free serum cholesterol. Esterified cholesterol concentration can be determined from the signal value of (1-4).

From the foregoing, it can be appreciated how various objects and features of the invention are met. The analyte test device is simple to use, typically requiring only placement of a single fluid sample on a filter strip. Where the test device is used as part of a signal reading and calculating apparatus, the desired analyte concentration value is obtained without additional sample-handling or calculation steps on the part of the user.

The analyte concentration value obtained is based on a standard curve which is corrected for background. That is, the assay is self-corrected for age and condition of the reagents, sample composition, and reaction conditions, such as temperature, which introduce uncertainty and variability in usual strip or solid-support-type assays. Further, only two signal values are needed to calculate the corrected, standardized assay value.

Although the invention has been described with reference to particular embodiments and uses, it will be understood that various changes and modifications can be made without departing from the invention.

It is claimed:

1. An assay device for determining the concentration of an analyte in an aqueous fluid sample containing the analyte and other solutes, comprising a first reaction zone containing analyte-specific component means effective, when an analyte-containing fluid sample is added to the zone, to utilize the analyte to produce a concentration of $H_2O_2$ which is dependent on the concentration of analyte present in the fluid sample, when the analyte concentration is below a concentration which is saturating with respect to the analyte-specific component, a second reaction zone containing (a) a known quantity of a reference compound which is not present in such aqueous fluid sample, and (b) reference compound-specific component means effective, when an analyte-containing fluid sample is added to the zone, to utilize the reference compound to produce a concentration of $H_2O_2$ which is dependent on the concentration of reference compound present in the second reaction zone, distributing means for delivering such fluid sample to each of the reaction zones, such that substantially the same analyte concentration is present in each reaction zone, when the fluid sample is applied to a single region of the distributing means, and contained in each of said first and said second reaction zones, a peroxidase enzyme and a dye which can be oxidized in the presence of said enzyme and $H_2O_2$ to a detectable product, at a concentration which is dependent on the concentration of $H_2O_2$ in the associated reaction zone, whereby the analyte-dependent signal generated by additional of sample to the first reaction zone can be corrected for (i) variations in signal level produced by the presence of such other solutes in the reaction zones and (ii) for the kinetics of the peroxidase-catalyzed oxidation of said dye from serum inhibition effects calculated from the second reaction zone.

2. The device of claim 1, wherein the reaction zones are porous-matrix zones designed to draw the fluid sample into the zones by surface wetting, and said distribution means includes a reservoir in contact with the two zones, for receiving and distributing the fluid sample to the reaction zones.

3. The device of claim 1, wherein said second reaction zone is composed of two layers, one containing the reference compound, and the other, said compound-specific component means.

4. The device of claim 1, which further includes a third reaction zone which contains said reference compound, in an amount which is different from that present in the said second zone, said compound-specific component means said peroxidase enzyme and said dye.

5. The device of claim 1, wherein said reference compound is a D-amino acid, and said compound-specific component means includes D-amino acid oxidase.

6. The device of claim 1, for determination of serum cholesterol, wherein said analyte-specific component means includes cholesterol ester hydrolase and cholesterol oxidase.

7. The device of claim 6, wherein said said reference compound is a D-amino acid, and said compound-specific component means includes D-amino acid oxidase.

8. The device of claim 6, for determination of total and free serum cholesterol only, which further includes a third reaction zone containing cholesterol oxidase, but not cholesterol esterase, and said compound-specific component means.

9. An apparatus for determining the amount of an analyte in an aqueous fluid sample containing the analyte and other solutes, comprising an assay device for determining the concentration of an analyte in an aqueous fluid sample, comprising (a) a first reaction zone containing analyte-specific component means effective, when an analyte-containing fluid sample is added to the zone, to utilize the analyte to produce a concentration of $H_2O_2$ which is dependent on the concentration of analyte present in the fluid sample, when the analyte concentration si below a concentration which is saturating with respect to the analyte-specific component, (b) a second reaction zone containing (i) a known quantity of a reference compound which is not present in such aqueous fluid sample, and (ii) reference compound-specific component means effective, when an analyte-containing fluid sample is added to the zone, to utilize the reference compound to produce a concentration of $H_2O_2$ which is dependent on the concentration of reference compound present in the second reaction zone, (c) distributing means for delivering such fluid sample to each of the reaction zones, such that substantially the same analyte concentration is present in each reaction zone, when the fluid sample is applied to a single region of the distributing means, and (d) contained in each of said first and said second reaction zones, a peroxidase enzyme and a dye which can be oxidized in the presence of said enzyme and $H_2O_2$ to a detectable product, at a concentration which is dependent on the concentration of $H_2O_2$ in the associated reaction zone, whereby an analyte-dependent signal generated by addition of sample to the first reaction zone can be corrected (i) for variations in signal level produced by the presence of such solutes in the reaction zones and for (ii) the kinetics of the peroxidase-catalyzed oxidation of said dye from serum inhibition effects calculated form the second reaction zone;

a signal detector for measuring such signal value in each of the reaction zones; and processor means for determining form the signal values of the reaction zones (a) the relationship between reference compound concentration and measured signal value, and (b) the concentration of analyte in the first reaction zone, using such determined relationship.

10. The apparatus of claim 9, wherein said the reaction zones are porous-matrix zones designed to draw the fluid sample into the zones by surface wetting, and said distributing means includes a reservoir in contact with the three zones, for receiving and distributing the fluid sample to the reaction zones.

11. The apparatus of claim 9, wherein said signal detector includes a light source for illuminating each zone with a light beam, and a beam detector for determining the intensity of reflectance of the beam from an illuminated zone.

12. The apparatus of claim 11, wherein said processor means is designed to determine (a) a corrected relationship between reference compound concentration and measured signal value, using the signal values measured in the second reaction zone, and (b) the concentration of analyte in the fluid sample, using the signal value measured in the first reaction zone and the corrected relationship between analyte concentration and measured signal value.

13. The apparatus of claim 10, for use in determining serum cholesterol, wherein said analyte-specific component means includes cholesterol ester hydrolase and cholesterol oxidase, for producing the intermediate reaction product $H_2O_2$ in the presence of cholesterol analyte, said compound-specific component means is effective to react with the reference compound to produce $H_2O_2$, and said signal-generating component means includes a peroxidase, and a dye which is converted by the peroxidase, in the presence of $H_2O_2$, to a distinctively colored, signal reaction product.

14. The apparatus of claim 13, wherein said reference compound is a D-amino acid, and said compound-specific component means includes the corresponding D-amino acid oxidase.

* * * * *